United States Patent [19]

Klein

[11] Patent Number: 5,348,268
[45] Date of Patent: Sep. 20, 1994

[54] HOUSING HOLDER FOR A MEDICAL MONITOR

[75] Inventor: Traugott Klein, Herrenberg, Fed. Rep. of Germany

[73] Assignee: Hewlett-Packard Company, Palo Alto, Calif.

[21] Appl. No.: 973,783

[22] Filed: Nov. 9, 1992

[30] Foreign Application Priority Data

Aug. 13, 1992 [DE] Fed. Rep. of Germany ... 9210835[U]

[51] Int. Cl.⁵ ............................................. F16M 11/00
[52] U.S. Cl. .................... 248/681; 248/221.3; 312/319.2; 312/248
[58] Field of Search ............... 248/681, 506, 220.2, 248/187, 689, 500, 680, 27.1, 655, 551, 225.2, 221.3, 221.4, 222.1; 312/319.2, 248

[56] References Cited

U.S. PATENT DOCUMENTS

| | | | |
|---|---|---|---|
| 2,600,748 | 6/1952 | Fox | 248/221.3 |
| 2,966,107 | 12/1960 | Sanderson | 248/187 |
| 3,430,906 | 3/1969 | Danz et al. | 248/310 X |
| 3,680,239 | 8/1972 | Andrews . | |
| 4,223,921 | 9/1980 | Goyne et al. | 248/221.3 X |
| 4,522,310 | 6/1985 | Mikic et al. | 248/221.3 X |
| 4,824,061 | 4/1989 | Sumikama et al. | 248/225.2 |
| 4,930,694 | 6/1990 | Yoshitake et al. | 248/222.1 X |
| 4,953,030 | 8/1990 | Seo | 248/221.4 X |
| 5,103,997 | 4/1992 | Shillington et al. | 248/221.4 X |
| 5,226,625 | 7/1993 | Hanna | 248/222.1 |

FOREIGN PATENT DOCUMENTS

| | | |
|---|---|---|
| 7441894 | 5/1973 | Fed. Rep. of Germany . |
| 3145310C2 | 11/1981 | Fed. Rep. of Germany . |
| 3339613A1 | 11/1983 | Fed. Rep. of Germany . |
| 3533419C2 | 9/1985 | Fed. Rep. of Germany . |
| 9010850.7 | 7/1990 | Fed. Rep. of Germany . |
| 4112052A1 | 4/1991 | Fed. Rep. of Germany . |
| 2183388A | 10/1985 | United Kingdom . |

Primary Examiner—Karen J. Chotkowski

[57] ABSTRACT

A housing holder for a medical monitor, which can be a cardiotocograph, includes a housing reception unit provided with several recesses. The monitor housing of the medical monitor has a plurality of protrusions provided on the back wall thereof, and arranged such that they are adapted to be inserted into the recesses of the housing reception unit. At least one of the protrusions has a stationary, downwardly directed projection for engagement with the side of the housing reception unit facing away from the monitor housing, the engagement being effected in the area of the respective recess. At least one additional protrusion is equipped with a spring-loaded snap member for engagement with the side of the housing reception unit facing away from the monitor housing, the engagement being effected in the area of another of the recesses.

10 Claims, 4 Drawing Sheets

HOUSING HOLDER FOR A MEDICAL MONITOR

FIELD OF THE INVENTION

The present invention refers to a housing holder for a medical monitor comprising a monitor housing. In a special case of use, the present invention deals with a housing holder for a cardiotocograph.

DESCRIPTION OF THE PRIOR ART

Cardiotocographs, which are constructed as so called antepartum monitors, serve to carry out prenatal medical supervision in the surgery of a gynecologist with his own practice. Hitherto used cardiotocographs had a substantial overall height so that they were exclusively suitable for installation on tables or transport trolleys in the surgery of the gynecologist. It is true that, more recently, antepartum monitors having a comparatively flat structural design in comparison with former monitors were put on the market, but the monitor housings of all these monitors were constructed such that the apparatus had to be placed on a table or on a transport trolley. This type of installation of the cardiotocograph will cause space problems in the surgery of the gynecologist, since also other devices, such as ultrasonic scanners, will have to be accommodated in close proximity to the physician in charge and the patients. In the case of such a cardiotocograph, the display devices and the control elements are arranged on the surface which is located opposite the base of the apparatus. Part of the display devices is defined by liquid-crystal display devices. It follows that, when the cardiotocograph lies flat on the transport trolley or on the table, the physician in charge will find it difficult to read the displays without rising from his chair and bending over the apparatus for this purpose. Similar problems will arise upon reading current measured values of a graph plotter, which is used for recording measured curves and which is provided in the interior of the cardiotocograph.

SUMMARY OF THE INVENTION

It follows that, taking this prior art as a basis, it is a major object of the invention to provide a housing holder for a medical monitor, which will facilitate operation of the medical monitor, improve the readability of the monitor display devices, and permit a mode of installation of said medical monitor which is better adapted to the spatial conditions in a medical surgery.

This task is solved by a housing holder for a medical monitor comprising a monitor housing, wherein the housing holder is provided with a housing reception unit having at least two recesses, the monitor housing has at least two protrusions, which are provided on the back wall thereof and which are arranged such that they are adapted to be inserted into the recesses of the housing reception unit, at least one of said at least two protrusions has a stationary, essentially downwards directed projection for engagement with the side of the housing reception unit facing away from the monitor housing, said engagement being effected in the area of one of said recesses, and at least one additional of said at least two protrusions is equipped with a spring-loaded snap means for engagement with the side of the housing reception unit facing away from the monitor housing, said engagement being effected in the area of another one of said recesses.

The housing holder according to the present invention is provided with a housing reception unit having at least two recesses. The monitor housing has at least two protrusions, which are provided on the back wall thereof and which are arranged such that they are adapted to be inserted into the recesses of the housing reception unit. At least one of said at least two protrusions has a stationary, essentially downwards directed projection for engagement with the side of the housing reception unit facing away from the monitor housing, said engagement being effected in the area of one of said recesses of the housing reception unit. At least one additional of said at least two protrusions is equipped with a spring-loaded snap means for engagement with the side of the housing reception unit facing away from the monitor housing, said engagement being effected in the area of another one of said recesses.

The housing holder according to the present invention permits the medical monitor to be attached to the wall, or to be supported such that it is inclined at an angle relative to the horizontal. With the aid of the structural design of the housing holder according to the present invention, the medical monitor is connected to the housing reception unit in a two-step fastening operation, e.g. by attaching first two protrusions with a stationary, downwards directed projection to opposite recesses of the housing reception unit, the major part of the weight of the medical monitor being already supported by the housing reception unit in this fastening step. Subsequently, the medical monitor will be pivoted by the operator about these stationary, downwards directed projections, which are in engagement with e.g. two recesses of the housing reception unit, until the preferably two additional protrusions equipped with the spring-loaded snap means will snap into engagement with the side of the housing reception unit facing away from the monitor housing, said engagement being effected in the area of the other recesses. The attachment of the monitor to the housing reception unit in two steps, which is conditioned by the structural design of the housing holder according to the present invention, offers the advantage that, when this comparatively heavy and expensive medical apparatus is removed from the housing holder, it cannot drop, when the locking engagement has been released by opening the snap means against their spring loading, but will be supported relative to the housing reception unit by the protrusions with the stationary projections.

The embodiment of the housing reception unit as a wall-mounted holder and the embodiment of said housing reception unit as an angular support holder will both improve the readability of the display devices and facilitate the operability of control elements provided on the front side of the apparatus, which is located opposite to the base thereof. The angular support holder and, especially, the wall-mounted holder will also provide a space-saving mode of accommodation of the medical monitor.

Although different embodiments of the snap means are imaginable, said snap means is, according to a preferred further development of the present invention, arranged such that it is movable in a sliding guide rail, which is formed on the inner side of the back wall of the monitor housing. This structural design of the snap means permits its realization on the basis of a production expenditure which is only insignificantly higher than that required when a standard monitor housing is being produced.

In accordance with an additional aspect of the invention, the snap means includes a downwards directed hook, which is provided with a ramp surface for an edge of the complementary recess of the housing reception unit, said ramp surface being arranged such that it extends at an angle to the plane of the back wall of the monitor housing, and said snap means being provided with a spring, which is arranged between the hook and the monitor housing and by means of which said hook is spring loaded. This structural design of the snap means guarantees a reliable automatic engagement, when the above-described second step of the two-step attachment operation is carried out, so that the monitor housing will reliably be locked in position relative to the housing reception unit.

The snap means preferably includes an actuating member, which is connected thereto so as permit unlocking of said snap means against the effect produced by the spring loading.

In accordance with another aspect of the invention, the actuating member is connected to the snap means in an area of said snap means located within the monitor housing and it extends through a wall of the monitor housing. The major part of the snap means will thus be positioned within the monitor housing and will be protected by said housing, although the snap means can be unlocked without any necessity of opening the housing.

An additional further development of the housing holder according to the present invention is to be seen in the features that the back wall of the monitor housing defines between its upper area and its lower area a receding step extending in the direction of the inner side of the monitor housing, and that, in addition, the housing reception unit defines between its upper area and its lower area a projecting step, which extends in the direction of the monitor housing and which is located below the step in the back wall of the monitor housing in spaced relationship therewith. This structural design will have the effect that a free space is defined between the back wall of the monitor housing and the front side of the housing reception unit in the central area of the monitor housing, said free space permitting the operator to take hold of the monitor housing in a convenient area thereof upon attaching the monitor housing to the housing reception unit or upon removing it therefrom. In other words, this structural design of the housing holder permits the operator to take hold of the monitor housing securely with both hands, when he attaches said monitor housing to the housing reception unit or removes it therefrom.

In accordance with an additional further aspect of the invention, particularly simple gripping of the monitor housing from behind is possible on the basis of the features that the depth of the steps is at least 1.2 cm, preferably 1.5 cm, and that the distance between the steps is at least 6 cm, preferably 8.5 cm.

In the case of this structural design of the monitor housing and of the housing reception unit, safe and easily handled unlocking is permitted in accordance with an additional further development on the basis of the feature that the actuating member of the snap means extends through an opening in the step in the back wall of the monitor housing in the free space defined at this location so that the operator's hand can take hold of the monitor housing. It follows that, when the monitor housing is removed from the housing reception unit, the operator can first fully take hold of the monitor housing, whereupon he will operate with one finger of each hand one of the preferably two actuating members for unlocking the snap means, and following this, the monitor housing will be pivoted about its stationary projections in a direction away from the housing reception unit before it is completely detached therefrom.

An additional further aspect of the invention is to be seen in the feature that the protrusions are defined by foot members of the monitor housing.

An additional preferred embodiment is established by the feature that the housing reception unit is provided with supporting surfaces for the protrusions of the monitor housing in the area of the recesses, said supporting surfaces being arranged behind the recesses with respect to the monitor housing. In combination with the stationary projection of the at least one protrusion and the spring-loaded snap means of the at least one additional protrusion, this structural design of the housing reception unit will have the effect that the monitor housing is fully fixed in position relative to the housing reception unit.

Preferably, the medical monitor is a cardiotocograph.

BRIEF DESCRIPTION OF THE DRAWINGS

In the following, two preferred embodiments of the housing holder according to the present invention will be explained in detail with reference to the drawings enclosed, in which.

DESCRIPTION OF THE PREFERRED EMBODIMENTS OF THE INVENTION

Figure 1:
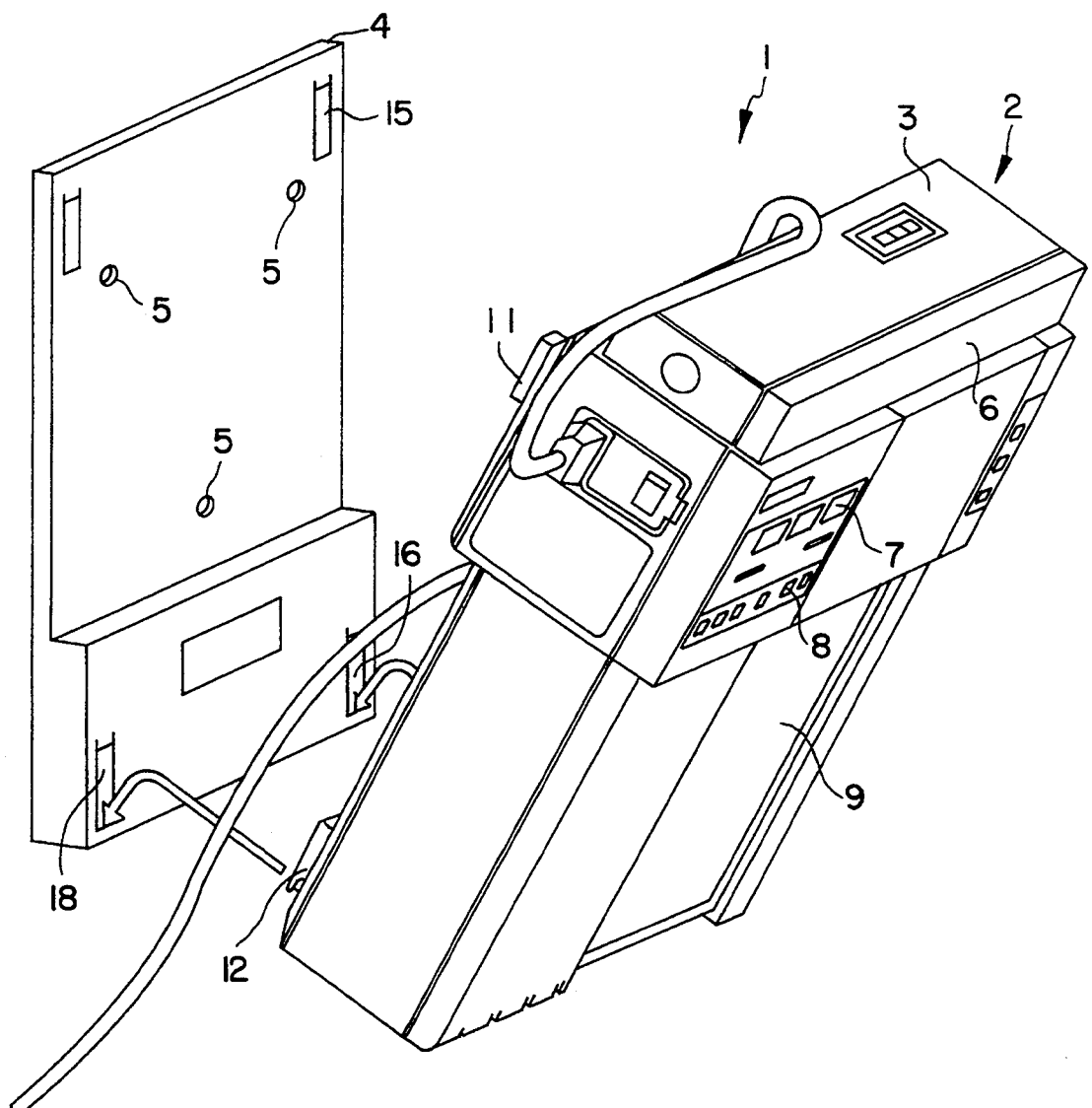
FIG. 1 shows a first embodiment of the housing holder according to the present invention.
Figure 4:
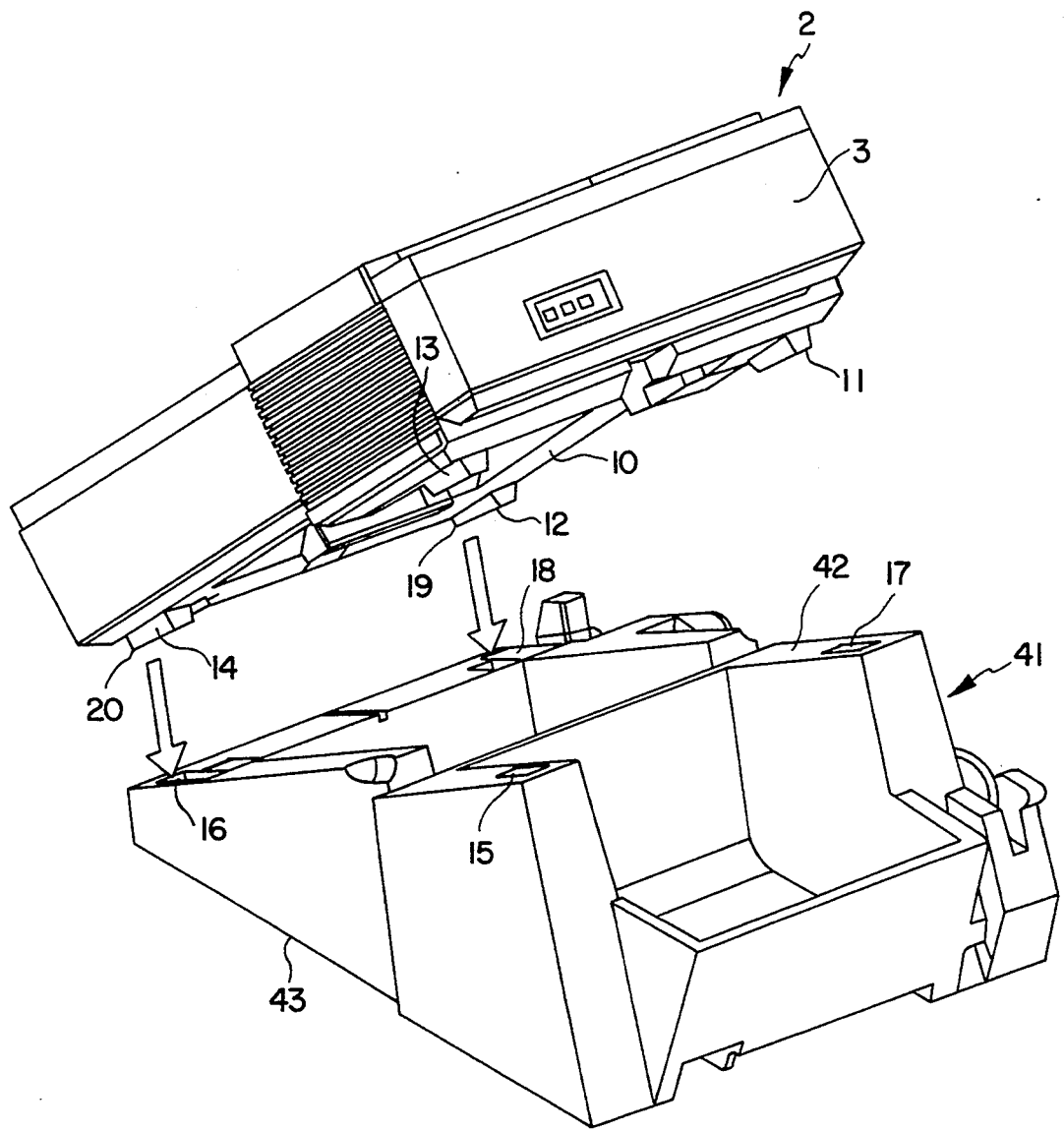
FIG. 4 shows a housing holder according to a second embodiment of the present invention.

As can be seen in FIG. 1, the housing holder according to the present invention, which is provided with reference numeral 1 in its entirety and a first embodiment of which is shown in said FIG. 1, comprises a medical monitor in the form of a cardiotocograph 2 including a monitor housing 3 as well as a housing reception unit 4, which is constructed as a wall-mounted holder in the case of the first embodiment shown in said figure. The wall-mounted holder 4 is fastened to the wall, which is located behind said wall-mounted holder 4, by means of three fastening screws 5 and by means of dowels (not shown). Various liquid-crystal display devices 7 as well as operating switches 8 are arranged on the monitor housing 3 of the cardiotocograph 2 primarily in the area of the front side or operating side 6. Furthermore, a paper ejection area 9 of a graphic plotter, which is accommodated in the interior of the cardiotocograph 2, is located on said operating side 6. As will especially be evident from the representation of the second embodiment of the housing holder according to the present invention which is shown in FIG. 4, but which uses, in comparison with FIG. 1, an identical cardiotocograph, the back wall 10 of the monitor housing 3 is equipped with four protrusions defined by four feet 11, 12, 13, 14 of the housing. The wall-mounted holder 4 is provided with four recesses 15, 16, 17, 18, which are arranged such that the feet 11, 12, 13, 14 of the housing can be inserted therein. In order to facilitate mutual alignment upon inserting the feet 11, 12, 13, 14 of the housing into the recesses 15, 16, 17, 18, said feet 11, 12, 13, 14 have a trapezoidal cross-sectional configuration.

Figure 2:
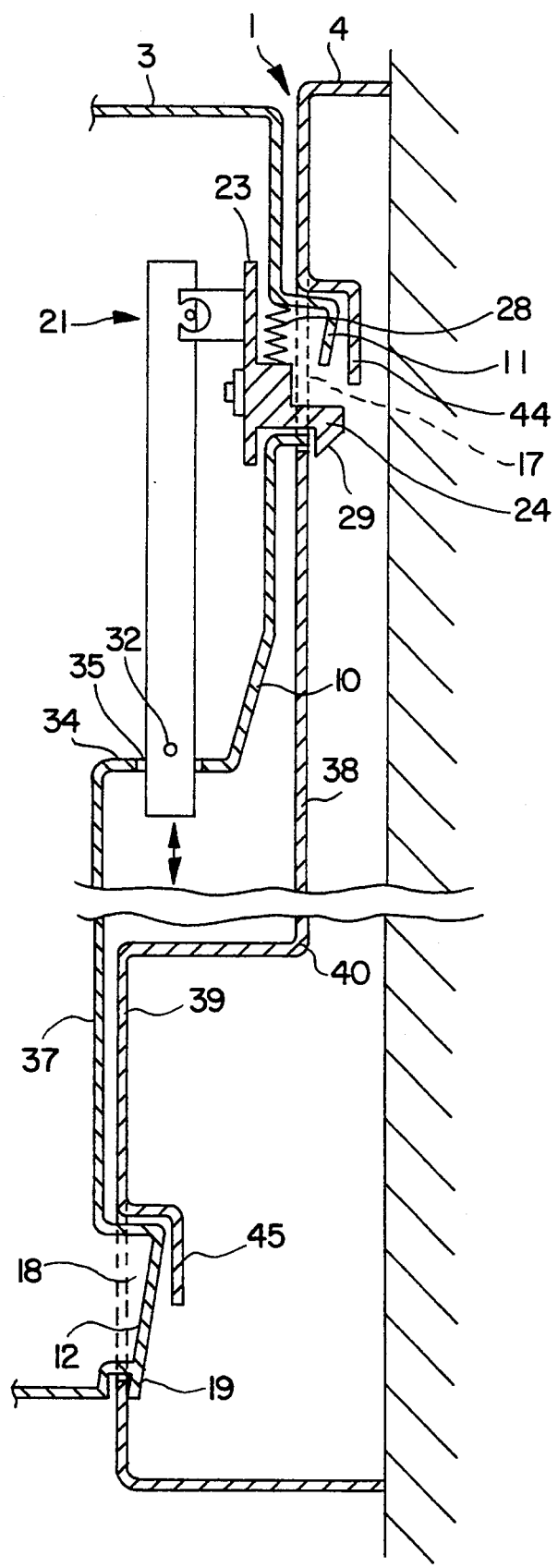
FIG. 2 shows a vertical sectional view of an essential part of the housing holder according to the present invention in accordance with the first embodiment.

As can especially be seen from the vertical sectional view of FIG. 2, the lower two feet 12, 14 of the monitor housing 3 have stationary projections 19, 20, which are directed downwards when the monitor housing is arranged in a vertical position.

In the area of the two upper feet 11, 13 of the housing, snap means are arranged, which are provided with reference numerals 21 and 22 in their entirety. As will be explained in detail hereinbelow, the snap means 21, 22 are spring loaded downwards and they are used for engagement with the side of the wall-mounted holder 4 facing away from the monitor housing 3, said engagement being effected in the area of the respective associated upper reception means 15, 17.

Each snap means 21, 22 comprises a downwardly directed hook 24, which is formed integrally with a sliding foot member 23 and which is guided on two sliding rails 25, 26 by means of said sliding foot member 23, as can especially be seen in the top view representation of part of the inner side of the back wall 10 of the monitor housing 3. The sliding rails 25, 26 are constructed as an integral component of the back wall 10 and they are arranged such that the hook 24 extends through the interior of the foot 11 of the housing. A hold-down device 27 engages the sliding foot member 23 from above so as to hold it on the sliding rails 25, 26. The hook 24 is provided with a bore (not shown) located below the sliding foot member 23 and used for holding a pressure spring 28, as can especially be seen in the top view of FIG. 3 in the case of which the relevant portion of the sliding foot member 23 has been broken away for the sake of clarity. The spring is located in the plane of the back wall 10 and is arranged in such a way that the hook 24 will be pressed downwards in the position shown in FIG. 2. The hook 24 is provided with an oblique ramp surface 29 for the edge 30 of the recess 17 onto which it will snap from above for establishing a position of engagement with the side of the wall-mounted holder 4 facing away from the monitor housing 3. An arm member 30 is formed integrally with the sliding foot member 23, said arm member 30 being brought into engagement with a pin 31 of an actuating member 33. In the position shown in FIG. 2, the actuating member 33 extends from the arm member 30 essentially vertically downwards through an opening 35 in a step 34 of the back wall 10 of the monitor housing 3. On the inner side of the step 34, the downward movement of the actuating member 33 is limited by an additional pin 32 in the position shown in FIG. 2.

As can be seen in detail in FIG. 2, the back wall 10 of the monitor housing 3 extends from an upper area 36 to a lower area 37 via the receding step 34 extending in the direction of the inner side of the monitor housing 3.

The wall-mounted holder 4 extends from its essentially planar upper area 38 to its lower area 39 via a projecting step 40 extending in the direction of the monitor housing 3, said two steps 34, 40 being vertically spaced from each other by at least 6 cm, preferably approx. 8.5 cm. The depth of the two steps is at least 1.2 cm, preferably approx. 1.5 cm. Hence, a manipulation space is defined between the two steps 34, 40, the lower area 37 of the monitor housing 3 and the upper area 38 of the wall-mounted holder 4; an operator can stretch his fingers into this manipulation space for taking hold of the monitor housing 3 with both hands and for operating in this position the actuating members 33 with both forefingers so as to unlock the two snap means 21, 22. When the snap means 21,22 have been unlocked, the cardiotocograph 2 will pivot about the stationary projections 19, 20 towards the operator, the cardiotocograph 2 being prevented from falling down when the snap means 21, 22 have been unlocked.

In this pivotal position, which corresponds e.g. to the position according to FIG. 1, the stationary projections 19, 20 of the two lower feet 12, 14 of the housing can be brought out of engagement with the recesses 16, 18 of the wall-mounted holder 4. The manipulations required for attaching the cardiotocograph 2 to the wall-mounted holder 4 are, consequently, carried out in reverse order.

The holders 4, 41 are provided with supporting surfaces 44, 45 for the protrusions 11, 12, 13, 14 of the monitor housing 3 in the area of the recesses 15, 16, 17, 18, said supporting surfaces 44, 45 being arranged behind said recesses 15, 16, 17, 18 with respect to the monitor housing 3.

Figure 3:
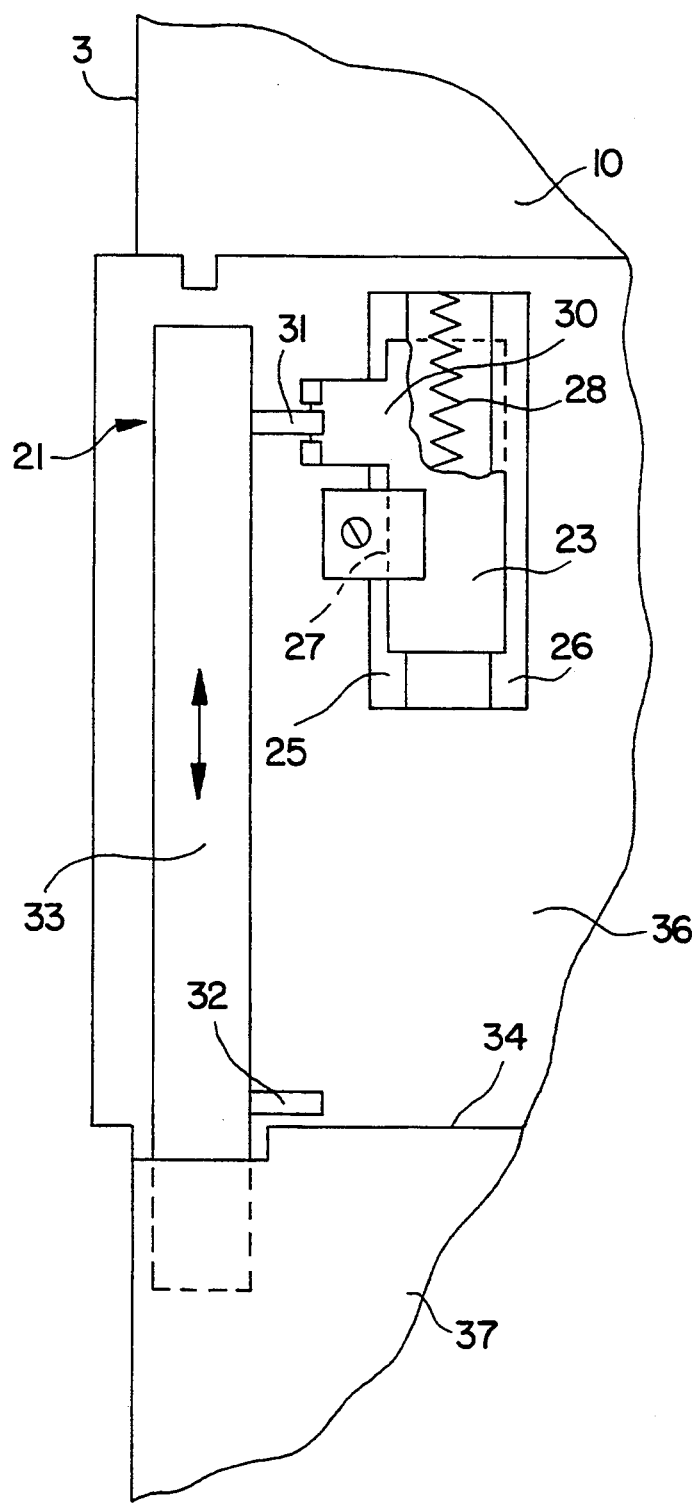
FIG. 3 shows an interior view of an essential part of a monitor housing back wall of the housing holder according to the first embodiment.

In the case of the embodiment described with reference to FIGS. 1 to 3, the housing reception unit has the form of a wall-mounted holder 4. For the purposes which are to be achieved by the present invention, it is, however, just as well possible to construct the housing reception unit such that the supporting area thereof is not defined by a vertical, but by a horizontal plane. An example of such a structural design of a housing reception unit is shown in FIG. 4, which shows a housing reception unit in the form of an angular support holder 41. With the exception of the deviations explained hereinbelow, the angular support holder 41 corresponds to the wall-mounted holder 4; identical or similar parts or areas being provided with identical reference numerals so that a renewed description of these parts or areas can be dispensed with.

In the case of the angular support holder 41, a supporting plane 42 for the monitor housing 3 extends at an angle of e.g. 30° relative to the horizontal, which is defined by a base 43 of the angular support holder 41. The above-mentioned angle can also be chosen much larger so as to permit an almost vertical support of the monitor housing 3, if this is desired in a particular case.

In the case of the embodiments shown, the housing reception unit 4, 41 is in each case provided with four recesses, protrusions in the form of feet 11, 12, 13, 14 of the housing representing components which are complementary to said recesses. To the person skilled in the art, it will be obvious that the number of protrusions provided on the monitor housing 3 and the corresponding number of recesses provided in the housing reception unit 4, 14 can be any number greater than or equal to two.

In the case of the embodiments shown, the protrusions of the monitor housing 3 simultaneously define the feet of said housing. However, deviating from this structural design, it is also possible to construct the protrusions as housing elements which are separate from the feet of the housing.

In the case of the embodiments shown, the protrusions equipped with the stationary projections are arranged in a lower area of the monitor housing 3 and the protrusions provided with the snap means are arranged in an upper area of the monitor housing. It is, however, just as well possible to arrange the protrusions equipped with the stationary projections in an upper area of the monitor housing and to arrange the snap means in a lower area of the housing, consequently. In this case, the sequence of movements taking place when the monitor housing 3 is fixed with respect to the housing reception unit 4, 41 will change insofar as the stationary, downward directed projections of the monitor housing 3 will first be attached to the upper recesses of the housing reception unit 4, 41, whereupon the lower portion of said monitor housing will be pivoted towards said housing reception until the snap means will snap in position.

In the case of the embodiment shown, the hook of the snap means 21, 22 is directed downwards. This is by no means absolutely necessary. A functionally corresponding result will also be obtained, when the hooks of the snap means are directed upwards and are spring loaded in a direction opposite to the direction used in the case of the embodiment shown, or when the hooks are arranged in the plane of the back wall 10 of the monitor housing 3 such that they can undergo antiparallel displacement in the horizontal direction and are spring loaded in opposite directions.

I claim:

1. A medical apparatus comprising:

a housing reception unit having at least two recesses;

a medical monitor having a monitor housing with at least two protrusions which are provided on a back wall thereof and which are arranged such that they are adapted to be inserted into the recesses of the housing reception unit;

at least one of said protrusions having a stationary, essentially downwardly directed projection for engagement with a side of the housing reception unit facing away from the monitor housing, the engagement being effected in the area of at least one the recesses;

at least one additional of said protrusions being equipped with a snap means for engagement with the side of the housing reception unit facing away from the monitor housing, such engagement being effected in the area of another one of the recesses, the snap means including a downwardly directed hook which is provided with a ramp surface for an edge of a complementary recess of the housing reception unit, the ramp surface being arranged such that it extends at an angle to a plane of the back wall of the monitor housing, the snap means further including a spring which is arranged between the hook and the monitor housing and by means of which said hook is spring loaded in the downward direction;

the back wall of the monitor housing defining between its upper area and its lower area a receding step extending in the direction of an inner side of the monitor housing;

the housing reception unit defining between its upper area and its lower area a projecting step which extends in the direction of the monitor housing and which is located below the receding step in the back wall of the monitor housing in spaced relationship therewith; and an actuating member connected to the snap means in an area of said snap means located within the monitor housing and extending through an opening in the step in the back wall of the monitor housing, said actuating member being arranged for unlocking the snap means against its spring loading.

2. A medical apparatus according to claim 1 wherein the snap means is arranged such that it is movable in a lateral direction in a sliding guide rail which is formed on the inner side of the back wall of the monitor housing.

3. A medical apparatus according to claim 1 wherein the depth of the steps is at least 1.2 cm, and the distance between the steps is at least 6 cm.

4. A medical apparatus according to claim 3 wherein the depth of the steps is at least 1.5 cm and the distance between the steps is at least 8.5 cm.

5. A medical apparatus according to claim 1 wherein the protrusions are defined by foot members of the monitor housing.

6. A medical apparatus according to claim 1 wherein the housing reception unit is constructed as a wall-mounted holder for holding the monitor housing in an essentially vertical position.

7. A medical apparatus according to claim 1 wherein the housing reception unit is constructed as an angular support holder for supporting the monitor housing in an inclined position relative to a horizontal base of the angular support holder.

8. A medical apparatus according to claim 1 wherein the housing reception unit is provided with supporting surfaces arranged behind said recesses with respect to the monitor housing.

9. A medical apparatus according to claim 1 wherein the medical monitor is a cardiotocograph.

10. A medical apparatus according to claim 1 further comprising an additional snap means which is spatially separated from the snap means mentioned above, both the additional snap means and the snap means being arranged such that they can be individually operated.

* * * * *